United States Patent [19]

Achini et al.

[11] 4,235,921
[45] Nov. 25, 1980

[54] TREATING MUSCULAR SPASMS AND CONVULSIONS WITH 3-AZABICYCLO[3.1.0]HEXANES

[75] Inventors: Roland Achini, Therwil; Wolfgang Oppolzer, Thônex; Beat Gähwiler, Münchenstein, all of Switzerland

[73] Assignee: Sandoz Ltd., Basel, Switzerland

[21] Appl. No.: 921,512

[22] Filed: Jul. 3, 1978

Related U.S. Application Data

[63] Continuation of Ser. No. 746,605, Dec. 1, 1976, abandoned.

[30] Foreign Application Priority Data

Dec. 2, 1975 [CH] Switzerland ............. 15643/75

[51] Int. Cl.$^3$ ............. A61K 31/40; C07D 209/52
[52] U.S. Cl. ............. 424/274; 260/326.27; 260/326.5 B; 260/326.62
[58] Field of Search ............. 260/293.54, 326.27; 424/267, 274

[56] References Cited

FOREIGN PATENT DOCUMENTS 1054088  4/1959  Fed. Rep. of Germany ...... 260/293.54

OTHER PUBLICATIONS

Chemical Abstracts, 77, 14807y (1972), [Rowland, I. et al., Chem.-Biol. Interactions, 4(6), 377–88 (1972)].

Primary Examiner—Henry R. Jiles
Assistant Examiner—Richard A. Schwartz
Attorney, Agent, or Firm—Gerald D. Sharkin; Robert S. Honor

[57] ABSTRACT

The present invention provides compounds of formula I,

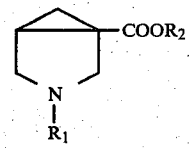

wherein
$R_1$ is hydrogen; alkyl of 1 to 5 carbon atoms; cycloalkyl of 5 to 7 carbon atoms; alkyl of 1 to 4 carbon atoms mono-substituted by cycloalkyl of 3 to 7 carbon atoms; phenylalkyl of 7 to 11 carbon atoms in the aggregate thereof, wherein the phenyl ring is unsubstituted or mono-substituted by halogen of atomic number from 9 to 35, alkyl of 1 to 4 carbon atoms; or alkoxy of 1 to 4 carbon atoms; alkenyl of 3 to 5 carbon atoms, wherein the multiple bond is other than in the $\alpha,\beta$ position; or 2-hydroxyethyl, and
$R_2$ is hydrogen or alkyl of 1 to 4 carbon atoms, having GABA-like activity.

21 Claims, No Drawings

TREATING MUSCULAR SPASMS AND CONVULSIONS WITH 3-AZABICYCLO[3.1.0]HEXANES

This is a continuation, of application Ser. No. 746,605 filed Dec. 1, 1976, now abandoned.

The present invention relates to azabicyclo [3,1,0]-hexane derivatives.

The present invention provides compounds of formula I,

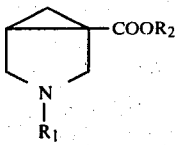

wherein
$R_1$ hydrogen; alkyl of 1 to 5 carbon atoms; cycloalkyl of 5 to 7 carbon atoms; alkyl of 1 to 4 carbon atoms mono-substituted by cycloalkyl of 3 to 7 carbon atoms; phenylalkyl of 7 to 11 carbon atoms in the aggregate thereof, wherein the phenyl ring is unsubstituted or mono-substituted by halogen of atomic number from 9 to 35, alkyl of 1 to 4 carbon atoms; or alkoxy of 1 to 4 carbon atoms, alkenyl of 3 to 5 carbon atoms, wherein the multiple bond is other than in the $\alpha, \beta$ position; or 2-hydroxyethyl, and
$R_2$ is hydrogen or alkyl of 1 to 4 carbon atoms.

$R_1$ is preferably hydrogen, alkyl, cycloalkyl, cycloalkylalkyl, phenylalkyl, mono-substituted phenylalkyl or 2-hydroxyethyl, and especially alkyl.

$R_2$ is preferably hydrogen.

In cycloalkylalkyl, the cycloalkyl moiety thereof has preferably 3, 5 or 6 carbon atoms, especially 3 carbon atoms, and the alkyl moiety thereof preferably has 1 or 2 carbon atoms, especially one carbon atom. Cycloalkyl of 5 to 7 carbon atoms has preferably 5 or 6, especially 5 carbon atoms. Phenylalkyl has preferably 7 to 9, especially 7 carbon atoms. Alkyl and alkoxy have preferably 1 to 2 carbon atoms, especially 1 carbon atom. Alkenyl has preferably 3 carbon atoms. Halogen is preferably chlorine or bromine.

The present invention provides a process for the production of a compound of formula I, as defined above, which comprises solvolysing a compound of formula II,

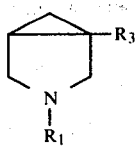

wherein
$R_1$ is as defined above, and
$R_3$ is a group capable of being solvolysed to form a group $COOR_2$, wherein $R_2$ is as defined above.

The process may be effected in conventional manner for such solvolysis reactions, e.g. using solvolysis conditions for the conversion of a nitrile, amide or ester to a carboxylic acid, or for the conversion of a nitrile or iminoester to a carboxylic acid ester.

$R_3$ is preferably cyano. Alternatively, when $R_2$ is hydrogen, $R_3$ is preferably alkoxycarbonyl, wherein the alkoxy moiety has 1 to 4 carbon atoms, or when $R_2$ is alkyl of 1 to 4 carbon atoms, $R_3$ is preferably a group $—C(=NH)—OR_2$, wherein $R_2$ is alkyl of 1 to 4 carbon atoms. Ethoxycarbonyl is a preferred alkoxycarbonyl group and the group $—C(=NH)—OC_2H_5$ is a preferred group $—C(=NH)—OR_2$, wherein $R_2$ is alkyl. When $R_1$ and $R_2$ are both hydrogen, $R_3$ is especially alkoxycarbonyl having 1 to 4 carbon atoms in the alkoxy moiety thereof.

For the production of a carboxylic acid of formula I, the solvolysis is carried out in the presence of water. There may be present a water miscible solvent such as an alcohol, e.g. ethanol, n-amylalcohol or ethylene glycol, or an ether such as dioxane or tetrahydrofuran. Preferably a catalyst is present. Suitable catalysts are acidic catalysts, e.g. a strong mineral acid like sulphuric acid or hydrochloric acid. Alternatively, a basic catalyst such as an alkali metal hydroxide or an alkaline earth metal hydroxide may be used, e.g. KOH, NaOH, $Ba(OH)_2$. A basic catalyst is preferred when $R_1$ is alkenyl. Suitable temperatures may be from about 20° to about 120° C., preferably from about 80° to about 100° C.

For the production of a carboxylic acid ester of formula I, a controlled solvolysis is used. Preferably, an aqueous mineral acid such as hydrochloric acid or sulphuric acid as catalyst is present. As solvent there may be present an excess of the alkanol $R_2OH$, wherein $R_2$ is alkyl. Suitable temperatures may be from about 20° to about 120° C., preferably from about 40° to about 100° C.

The compounds of formula I may be isolated and purified in conventional manner.

Free base forms of the compounds of formula I may be converted into acid addition salt forms in conventional manner and vice versa. A suitable acid is hydrochloric acid. Free acid forms of compounds of formula I, wherein $R_2$ is hydrogen, may be converted into salt forms, e.g. the sodium salt, in conventional manner and vice versa.

The compounds of formula II may be produced in known manner. Of the starting materials of formula IIa,

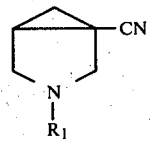

wherein $R_1$ is as defined above, the 3-methyl- and the 3-benzyl-3-azabicyclo[3.1.0]hexane-1-nitriles are known. The remaining compounds of formula IIa, except for 3-azabicyclo[3.1.0]hexane-1-nitrile and 3-(2-hydroxyethyl)-3-azabicyclo[3.1.0]hexane-1-nitrile may be prepared in conventional manner, e.g. in analogous manner to the known compounds of formula IIa, starting from the corresponding N-substituted 4-hydroxymethyl-3-pyrrolidine-carbonitrile.

By replacing the N-benzyl group of 3-benzyl-3-azabicyclo[3.1.0]hexane-1-carbonitrile by, for example, a 2,2,2-trichloroethoxycarbonyl group and reductively splitting off this group, or directly by selective hydrogenating the N-benzyl group, 3-azabicyclo[3.1.0]-hexane-1-carbonitrile may be obtained. Introduction of a 2-hydroxyethyl group in the last mentioned compound, e.g. using ethylene oxide, affords 3-(2-hydroxyethyl)-3-azabicyclo[3.1.0]hexane-1-nitrile.

The compounds of formula IIb,

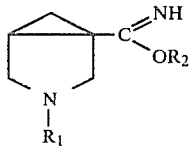

wherein $R_1$ and $R_2$ are as defined above, may be produced, for example, by treating a nitrile of formula IIa, as defined above, with an excess of an alcohol of formula $R_2OH$, wherein $R_2$ is alkyl, in the absence of water in the presence of an acid, e.g. dry gaseous hydrogen chloride. The compounds of formula IIb may be obtained in the form of the di-acid addition salt. If a nitrile of formula IIa is reacted with an aqueous mineral acid, e.g. aqueous hydrochloric acid or sulphuric acid, instead of dry gaseous hydrogen chloride, the resultant iminoester is converted directly into the carboxylic acid ester of formula I.

Compounds of formula IIc,

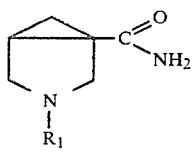

wherein $R_1$ is as defined above, may be made, for example, by controlled hydrolysis of the corresponding nitrile or by aminolysis of the corresponding ester with ammonia.

Insofar as the preparation of any starting material is not particularly described, these compounds are known or may be produced and purified in accordance with known processes or in a manner analogous to processes described herein or to known processes.

In the following Examples all temperatures are in degrees Centigrade and are uncorrected.

EXAMPLE 1

3-Methyl-3-azabicyclo[3.1.0]hexane-1-carboxylic acid ethyl ester

Crude 3-methyl-3-azabicyclo[3.1.0]hexane-1-carboximidic acid ethyl ester dihydrochloride (obtained as described below) is boiled under reflux for 3 hours in 30 ml of ethanol and 0.6 ml of water. After evaporation, the resultant residue is made alkaline with an aqueous sodium bicarbonate solution. Extraction with methylene chloride gives the title compound (M.Pt. of napthalene-1,5-disulphonate 161°–165°).

The starting material is obtained as follows:

A solution of 4.45 g of 3-methyl-3-azabicyclo[3.1.0-]hexane-1-carbonitrile in 45 ml of ethanol is saturated, under ice-cooling, with HCl gas, and then finally boiled for 15 hours under reflux to form a mixture containing the starting material which is isolated by evaporation of the mixture and used further as such.

EXAMPLE 2

3-Methyl-3-azabicyclo[3.1.0]hexane-1carboxylic acid

A solution of 10 g of 3-methyl-3-azabicyclo[3.1.0]-hexane-1-carboxylic acid ethyl ester in 20 ml of ethanol is treated with a solution of 18.8 g of $Ba(OH)_2 \cdot 8H_2O$ in 500 ml of water. The resultant mixture is boiled under reflux for 15 hours. After cooling, the mixture is neutralized with 10% sulphuric acid. The resultant barium sulphate is filtered off. The filtrate is evaporated and taken up in methanol. After filtration through talc, the filtrate is concentrated to yield the title compound as crystals of M.Pt. 193°–195°.

EXAMPLE 3

3-Methyl-3-azabicyclo[3.1.0]hexane-1-carboxylic acid

A solution of 10 g of 3-methyl-3-azabicyclo[3.1.0]-hexane-1-carbonitrile is 60 ml of saturated ethanolic KOH and 20 ml of water is boiled under reflux for 15 hours. After neutralization with hydrochloric acid the mixture is evaporated and the title compound is extracted from the resultant dried residue with hot absolute ethanol (M.P. 193°–195°).

In analogous manner to that described in Example 1, 2 or 3 the following compounds of formula I may be obtained, wherein:

| Example No. | Analogous to Example No.* | $R_1$ | $R_2$ | M.Pt. |
|---|---|---|---|---|
| 4 | 2, 3 | benzyl | H | Amorphous |
| 5 | 2, 3 | H | H | 232°–234° (decomp.) |
| 6 | 2, 3 | cyclopentyl | H | 199°–201° |
| 7 | 2, 3 | 2-hydroxyethyl | H | 206°–208° |
| 8 | 2, 3 | ethyl | H | |
| 9 | 2, 3 | n-butyl | H | |
| 10 | 2, 3 | isopropyl | H | |
| 11 | 2, 3 | cyclopropylmethyl | H | |
| 12 | 1 | benzyl | ethyl | 160°–162° (hydrogen oxalate) |
| 13 | 1 | H | ethyl | 150°–151° (hydrogen fumarate) |
| 14 | 1 | cyclopentyl | ethyl | 156°–158° (hydrogen oxalate) |

*For compounds prepared in analogous manner to Example 1 the starting material is a compound of formula IIb, wherein $R_2$ is ethyl; for compounds prepared analogous to Example 2, a compound of formula I, wherein $R_2$ is ethyl and for compounds prepared analogous to Example 3, a compound of formula IIa.

Additionally, the following compounds of formula I, wherein $R_2$ is isopropyl, may be prepared, wherein $R_1$ is:

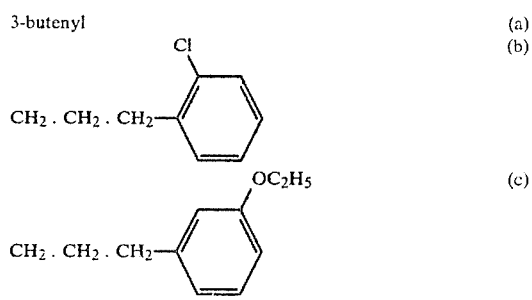

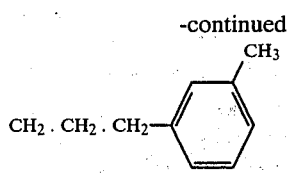

The compounds of formula I are useful because they exhibit pharmacological activity in animals. In particular, they exhibit GABA-like activity (GABA is gamma aminobutyric acid) as indicated in standard tests. For example, the compounds inhibit the spontaneous bioelectric acitivity of cerebellar Purkinje cells at concentrations of from about $10^{-7}$ M to about $10^{-3}$ M of the compounds in accordance with the principles of B. Gähwiller et al, Brain Research 53, 71, (1973), and 99, 85 (1975). Additionally, the inhibition is antagonised by Picrotoxin at a concentration of $10^{-4}$ M.

The compounds are therefore useful as agents for the treatment of cerebral disturbances, e.g. cerebral vascular disturbances such as cerebral insufficiency. Additionally, the compounds are useful for the treatment of muscular spasms, extrapyramidal disturbances, or convulsions, e.g. those associated with Huntington's chorea. The compounds are furthermore useful for the treatment of epilepsy.

For this use the dosage will, of course, vary depending on the compound employed, mode of administration and treatment desired. However, in general, satisfactory results are obtained when administered at a daily dosage of from about 0.01 mg to about 50 mg per kg animal body weight, conveniently given in divided doses 2 to 4 times a day or in sustained release form. For the larger mammals, the total daily dosage is in the range from about 1 to about 2000 mg (e.g. 20 to 2000 mg, or 1 to 1000 mg), and dosage forms suitable for oral administration comprise from about 0.25 mg to about 1000 mg of the compounds admixed with a solid or liquid pharmaceutical carrier or diluent.

The compounds of formula I may be administered in free form, in pharmaceutically acceptable acid addition salt form or, when $R_2$ is hydrogen, in pharmaceutically acceptable salt form. Such forms exhibit the same order of activity. The present invention also provides a pharmaceutical composition comprising a compound of formula I, in free form or in pharmaceutically acceptable acid addition salt form or, when $R_2$ is hydrogen, in pharmaceutically acceptable salt form, in association with a pharmaceutical carrier or diluent. Such compositions may be in the form of, for example, a solution or a tablet.

We claim:

1. A compound of formula I,

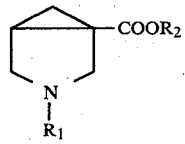

wherein $R_1$ is hydrogen; alkyl of 1 to 5 carbon atoms; cycloalkyl of 5 to 7 carbon atoms; alkyl of 1 to 4 carbon atoms mono-substituted by cycloalkyl of 3 to 7 carbon atoms; phenylalkyl of 7 to 11 carbon atoms in the aggregate thereof, wherein the phenyl ring is unsubstituted or mono-substituted by halogen of atomic number from 9 to 35, alkyl of 1 to 4 carbon atoms, or alkoxy of 1 to 4 carbon atoms; alkenyl of 3 to 5 carbon atoms wherein the multiple bond is other than in the $\alpha,\beta$ position; or 2-hydroxyethyl, and $R_2$ is hydrogen or alkyl of 1 to 4 carbon atoms, in free form, in pharmaceutically acceptable acid addition salt form or, when $R_2$ is hydrogen, in pharmaceutically acceptable salt form.

2. A pharmaceutical composition useful for treating muscular spasms or convulsions, in animals comprising a therapeutically effective amount of a compound of claim 1, in association with a pharmaceutical carrier or diluent.

3. A method of treating muscular spasms or convulsions, in animals which comprises administering to an animal in need of such treatment a therapeutically effective amount of a compound of claim 1.

4. A compound of claim 1, wherein $R_2$ is hydrogen.

5. A compound of claim 4, wherein $R_1$ is benzyl.

6. A compound of claim 4, wherein $R_1$ is H.

7. A compound of claim 4, wherein $R_1$ is cyclopentyl.

8. A compound of claim 4, wherein $R_1$ is 2-hydroxyethyl.

9. A compound of claim 4, wherein $R_1$ is ethyl.

10. A compound of claim 4, wherein $R_1$ is n-butyl.

11. A compound of claim 4, wherein $R_1$ is isopropyl.

12. A compound of claim 4, wherein $R_1$ is cyclopropylmethyl.

13. A compound of claim 1, wherein $R_2$ is ethyl.

14. A compound of claim 1, wherein $R_1$ is benzyl.

15. A compound of claim 1, wherein $R_1$ is H.

16. A compound of claim 1, wherein $R_1$ is cyclopentyl.

17. A compound of claim 1, which is 3-methyl-3-azabicyclo[3.1.0]hexane-1-carboxylic acid ethyl ester.

18. A compound of claim 1, which is 3-methyl-3-azabicyclo[3.1.0]hexane-1-carboxylic acid.

19. A compound of claim 1 wherein $R_1$ represents alkyl of 1-5 carbon atoms.

20. A compound of claim 4 wherein $R_1$ represents alkyl of 1-5 carbon atoms.

21. A compound of claim 4 wherein $R_1$ represents alkyl of 1-2 carbon atoms.

* * * * *